United States Patent
Boyer et al.

[11] Patent Number: 6,059,762
[45] Date of Patent: May 9, 2000

[54] MALE URINARY INCONTINENCE DEVICE

[76] Inventors: Mildred E. Boyer, 6910 Tipp-Cowlesville Rd.; Marinus B. Bosma, 5125 Studebaker Rd., both of Tipp City, Ohio 45371

[21] Appl. No.: 09/118,967

[22] Filed: Jul. 20, 1998

[51] Int. Cl.[7] ........................................ A61F 5/44
[52] U.S. Cl. ............................................. 604/349
[58] Field of Search ................... 604/327, 347, 604/349, 353, 350–352

[56] References Cited

U.S. PATENT DOCUMENTS

| | | | |
|---|---|---|---|
| 3,032,038 | 5/1962 | Swinn | 604/353 |
| 3,489,150 | 1/1970 | Glaude | 604/353 |
| 3,707,969 | 1/1973 | Sanford | 604/347 |
| 4,122,849 | 10/1978 | Dietz | 602/73 |
| 4,813,943 | 3/1989 | Smith | 604/329 |
| 5,009,649 | 4/1991 | Goulter et al. | 604/351 |
| 5,593,389 | 1/1997 | Chang | 604/174 |
| 5,797,890 | 8/1998 | Goulter et al. | 604/351 |

*Primary Examiner*—John G. Weiss
*Assistant Examiner*—Cain Mager
*Attorney, Agent, or Firm*—William Weigl

[57] ABSTRACT

A urinary incontinence device comprises a cover portion for male genitalia and a separable urine-collecting pouch. The cover portion has a frontal penis opening therethrough, a strap member encircling the wearer's body and securing the cover potion to the genitalia, a separate liquid-impervious pouch having an open, and means for removably attached the neck portion to the cover portion to enable a penis protruding through the cover portion opening to enter into the pouch. The pouch contains a liquid-absorbent media for suspension of liquid by the media, and preferably has a zipper lock on the side of the pouch opposite the cover portion opening to enable an active male to open the zipper and extend his penis therethrough for discharge of urine into a urinary receptacle.

8 Claims, 2 Drawing Sheets

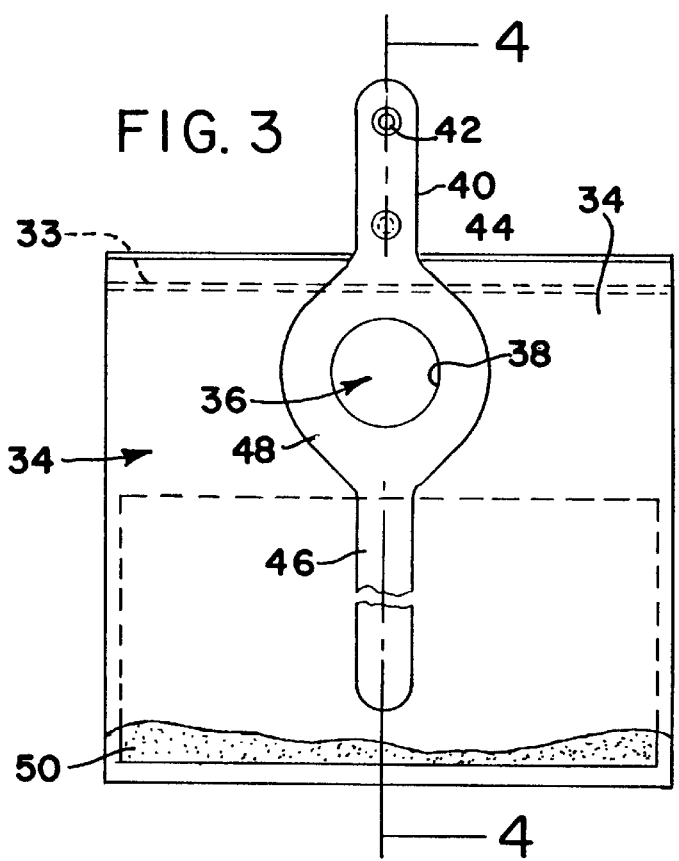
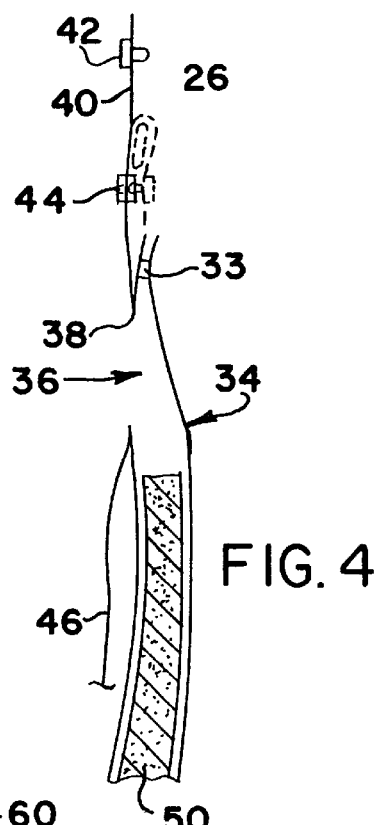
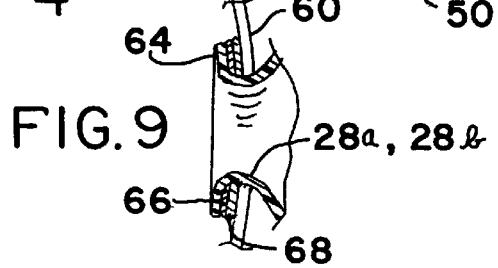
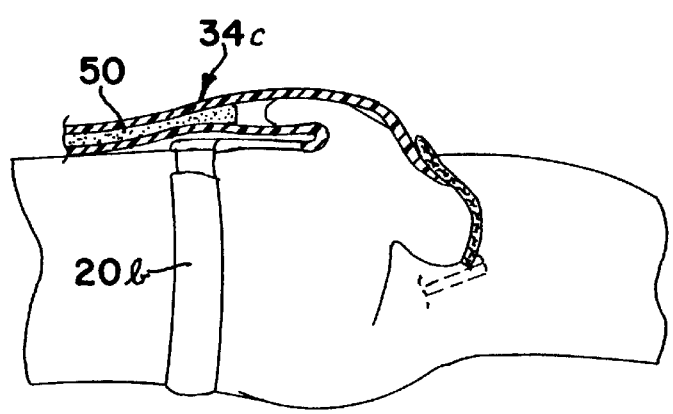
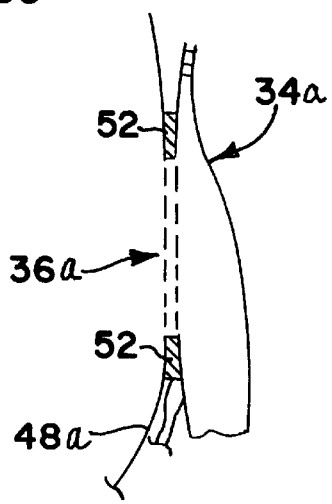

MALE URINARY INCONTINENCE DEVICE

This invention relates generally to a device for collecting urine from the penis of a human male, and in particular relates to such a device for use by a male individual whose bladder is uncontrollable, whether the individual is standing erect or is lying horizontally or inclined at the time of urine discharge. The invention may also be practical for use by continent males in instances where urinary receptacles are unavailable, or by male infants wearing diapers. This application is based on U.S. Provisional Patent Application Ser. No. 60/054,136 filed on Jul. 29, 1997.

BACKGROUND OF THE INVENTION

A large percentage of "shut-ins", i.e., individuals who stay in their residences or at least refuse or hesitate to go out in public and mingle with others, are believed to do so as a result of incontinence, the inability to control their bladders. Some such individuals may be bedridden, with the primary prevention of dripping or expelling urine being controlled by a catheter which is inserted into the urethra and anchored at the opening to the bladder. Such an invasive procedure often results in the development of infection. The catheter is connected via flexible tubing to a large collection bag which is typically located on the bedroom floor. Carrying of such a bag by the individual is ordinarily impractical because of its size.

Another solution to the problem has been provided by the so-called "Texas Catheter", which consists of a rubber sheath which covers the penis area and has a tube projecting from the penis. This tube is about the same resiliency and flexibility as a catheter. It may be connected to a bag strapped to the user's leg if the wearer is an active male, as compared to one who is bedridden. Not only is this device very expensive, but it is bulky as well. It can protrude outwardly from the wearer's trousers so as to cause personal embarrassment to the wearer as well as other individuals. The tube, while relatively soft and flexible, often projects in a manner to appear like an erect penis. In addition, the tube and rubber sheath are of one piece, requiring frequent washing of both to rid them of an unpleasant urine odor. If the rubber sheath is too tight about one's penis, it can restrict blood flow, or if too loose, it may fall off.

SUMMARY OF THE INVENTION

The invention provides a urine-collecting device for either a bedridden or an active male, whether collection is required as a result of the inability to exercise bladder control or because an active male does not have access to a urinary receptacle, such as while flying in a small, private airplane or where other conditions exist in which ordinary male urination is not an option.

The device comprises a cover portion for the male genitalia and a urine-collecting pouch. The cover portion has a frontal penis opening therethrough, a preferably detachable strap member encircling the wearer's body and securing the cover portion to the genitalia, a separate liquid-impervious pouch having an open neck portion for connection with the cover portion opening, and means for removably attaching the neck portion to the cover portion to enable a penis protruding through the cover portion opening to enter into the pouch, without being constricted. The pouch contains a liquid-absorbent media for suspension of liquid by the media, and preferably has a zipper lock on the side of the pouch opposite the cover portion opening to enable an active male to open the zipper and extend his penis therethrough for discharge of urine into a urinary receptacle. The ease with which the device may be changed makes cleansing of both the device and genitalia a simple matter.

A principal object of the invention is to provide a simple, inexpensive male urine-collecting device having a separable genitalia cover portion with an opening therethrough and a liquid-impervious pouch having a neck portion alignable with the cover portion opening to enable a wearer's penis to extend directly into the pouch, without being constricted, for capturing urine discharged through the penis.

An ancillary object is to allow such a device to be utilized while the wearer is standing, lying down or seated, thereby enabling use by either a bedridden or an active individual.

A further object is to enable use of the principles of the invention by males of any age, independent of whether or not the individual is incontinent.

Other objects will become apparent from the following description, in which reference is made to the accompanying drawings.

DESCRIPTION OF THE DRAWINGS

FIG. 3 is a fragmentary view of a pouch disconnected from a user, and is taken looking essentially from the left of FIG. 2 before connection to a suspensory.

FIG. 4 is a simplified cross-sectional view of a portion of the pouch looking in the direction of the arrows 4—4 of FIG. 3.

FIG. 5 is a section of a different form of means for attaching the pouch to the suspensory.

FIG. 8 is a cross-sectional view of a bedridden patient wearing the support means of FIG. 7 and permitting the pouch to lie on his stomach, facing toward the patient's head.

FIG. 9 is an enlarged fragmentary cross-sectional view of another form of means for attaching a pouch to a support.

DESCRIPTION OF THE PREFERRED EMBODIMENTS

Figure 1:
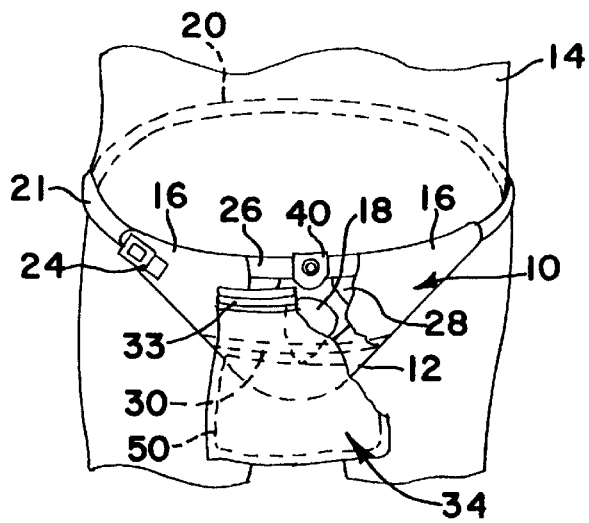
FIG. 1 is a frontal fragmentary view of a human male wearing one version of a means for supporting a removable, disposable urine-collecting pouch, this supporting means being commonly known as a testicular suspensory.

In FIG. 1, the support for male genitalia includes a conventional suspensory 10 of the type sold by Keep-Fit, Inc. of Cincinnati, OH., Model #2480. It includes as a primary element a testicle sack 12 made of air-pervious cloth having elastic material woven thereinto to enable the sack to surround and firmly contain the testicles while being suspended freely from a person's body 14. At opposite side and upper edges of the sack 12 are fastened side panels 16 which partially cover the groin areas on each side of the user's penis 18.

A strap member 20 surrounds the user's anatomy above his buttocks 22 and has a free end 21 provided with one portion of a snap fastener 24. The other portion of the fastener 24 is connected to the side panel 16 at the left of FIG. 1. It can thus be seen that the snap fastener allows for adjustability of the length of the strap member 20 to accommodate individuals of different girths. Obviously, in place of the snap fastener 24 as well as of other detachable elements to be described hereinafter, well-known Velcro fasteners or other attaching elements may be used.

Figure 2:
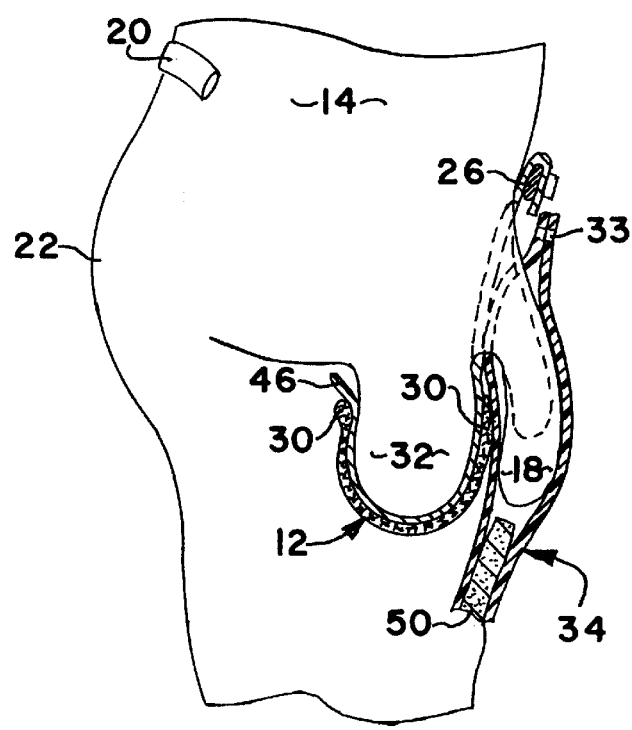
FIG. 2 is an enlarged side cross-sectional view of the suspensory of FIG. 1 and one embodiment of urine pouch mounted thereto.

A thin elastic band 26 extends across and is sewn to opposing inner upper edges of side panels 16, leaving an opening 28 below the band 26 and above a bead 30 which is essentially U-shaped to allow the user's penis to extend through the opening 28 as shown in FIGS. 1 and 2.

What has been described thus far is the conventional suspensory which encircles the user's testicles 32 and penis 18 and isolates them essentially as a ring to suspend them from the user's body.

Detachably mounted to the suspensory 10 by any of a variety of attachment means is a pouch 34 which may be essentially of the type of flat polyvinyl container used to contain and protect food in a refrigerator or freezer. It preferably has a liquid-retaining zipper lock 33 extending across the side of the pouch outwardly from the user, for purposes to become apparent. The pouch 34 has a neck portion 36 forming an opening 38 which is generally alignable with the opening 28 of the suspensory 10. The two openings, when aligned with the pouch 34 attached to the suspensory, encircle the penis adjacent its connection to the body. The pouch 34 may be pleated for expansion purposes if desired.

FIGS. 3 and 4 illustrate one simple technique for mounting the pouch 34 to the suspensory 10. Other techniques are easily within the design capabilities of persons skilled in this art. An upwardly-extending strap 40 with male and female elements 42 and 44 of a snap fastener may pass around the elastic band 26 as shown in dotted lines in FIG. 4. This may be the primary securing element of pouch 34 to suspensory 10. A downwardly-extending strap 46 may also be provided on an annular flange or annulus 48 which can be heat-sealed or otherwise mounted to one side of the pouch, to provide a penile opening through the annulus 48 and an opening in the side of the pouch to which annulus 48 is attached. Any conventional acceptable type or ply of absorbent panel 50 may be contained within the pouch 34 to suspend urine dripping or discharged from the penis.

A normal-sized flaccid adult penis is portrayed in full lines in FIG. 2. A smaller adult penis of a male of advanced age is shown in dotted lines in that same figure. Because the elastic suspensory opening so closely encircles the penis and encompasses the testicles, penis size, whether flaccid or erect, or whether the penis is adult-sized or infantile, is ordinarily immaterial. The concept should be equally adapted to a male infant, both as a money-saving procedure for the parents of the child where disposable diapers are used, and as an environmental savings where fewer diapers need be sent to a landfill waste disposal operation. For example, if urine is collected via this device from a male infant who is also wearing a disposable diaper, only the pouch and absorbent media need be disposed of, instead of throwing out the entire diaper each time the boy wets himself. The diaper may have to be replaced only after a bowel movement, and normally ought to be able to be kept in use after a mere wetting. Much concern has been expressed in environmental circles about the growing use of disposable diapers in industrialized countries and the inability to dispose of them in any fashion other than to deposit them in landfill areas. Under certain circumstances, this concept may also be applicable to pet animals such as dogs. The design should be one which prevents the animal from removing the device.

FIG. 5 illustrates a variation in design of the neck portion 36a of the pouch 34a, wherein the annulus 48a is connected to the pouch by use of a flexible washer 52 having a self-adhesive material on opposite sides to interconnect the pouch and annulus.

Figure 6:
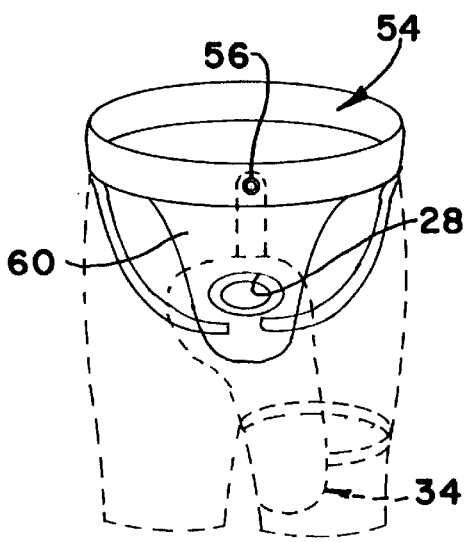
FIG. 6 is a view of a conventional-type athletic supporter with an opening therethrough for attaching a different form of pouch which lies against the leg of a user under his pantleg.

FIG. 6 illustrates a conventional jockstrap 54 modified to provide an opening 28a and one part 56 of a snap fastener. Through this opening 28a and with the part 56 of the fastener also being utilized with a strap like strap 40, a pouch like that of FIGS. 1–4 may be connected to catch urine discharge. If the person is active or mobile, a larger pouch 34b may be strapped to his thigh beneath his pantleg. Such a jockstrap 54 can be put on by pulling it up over his feet and legs before putting on his trousers.

Figure 7:
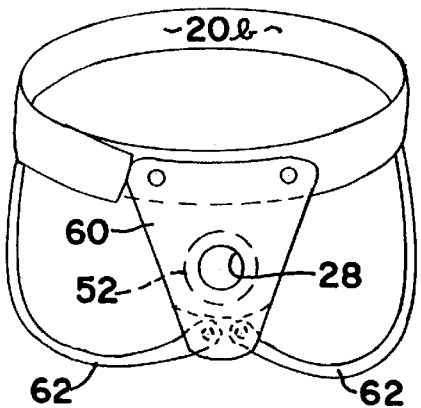
FIG. 7 is still another form of support means for a pouch and is primarily designed for use by a bedridden patient.

The jockstrap version of our invention would not be as easily usable by a bedridden man, such as one lying on his back after surgery, or one who is terminally ill and confined to a bed. Such a male is shown in FIG. 8, wearing yet another modification of the invention illustrated in FIGS. 7 and 8, one which is readily attachable to and detachable from an immobilized person. This version is somewhat similar to the jockstrap version of FIG. 6, but has a detachable strap member 20b, allowing part of the strap member to be slid beneath the patient while arching his back slightly. The strap member can then be brought around the waist and fastened at the front or side, preferably by Velcro, hook and loop means, or another suitable adjustable-girth means. A cover portion 60 having an opening 28b can be separable from both the strap member 20b and a pair of straps 62 extending over the buttocks of the wearer. This modification consists of three separable elements, the washable strap member 20b, the cover portion 60 and a pouch 34c which may be generally comparable to pouch 34 of FIG. 1. This allows a person lying on his back as in FIG. 8 to lay the pouch on his stomach or between or in front of his legs, in the general direction his flaccid penis can readily extend, while dripping into the pouch. Obviously, while lying on his back, depending of the patient's penis dimensions, there is greater risk of leakage onto the patient than there might be if the suspensory 10 is employed.

FIG. 9 illustrates a design alternative to the snap fastener means 42, 44 of FIGS. 3 and 4 for attaching a pouch to the cover portion 60. An annular rim 64 is provided on the pouch and is adapted to extend through the opening 28a or 28b toward the user. For this design, a pair of annular hook and loop fastener portions 66, 68 surround the opening, one being connected to the cover portion 60 and facing toward the user, and the other being connected to an inside surface of the rim 64 and facing outwardly away from the user. Once passed through the opening, the fastener portions 66 and 68 may be pressed toward each other to secure the pouch to the cover portion.

Various other changes may be made without departing from the spirit and scope of the claims.

Having described our invention, we claim:

1. A device for use by a human male in collecting urine from a user's penis,
    said device including:
        a strap member for encircling the user's back and snuggly gripping at least that portion of the user's anatomy above his buttocks to secure the strap to the user's body;
        a genital cover portion connected to the strap member for supporting the user's genitals, said cover portion including a frontal opening for receiving and enabling the user's flaccid penis to protrude outwardly through said frontal opening;

a pouch having an open neck portion, said pouch having a depending liquid-impervious urine-collecting portion of sufficient flexibility to conform with and be retained essentially against the user's body;

an absorbent material loosely provided within said pouch for suspending liquid urine in said material;

a zipper in said pouch for enabling saturated absorbent material to be removed and replaced; and, each of said neck portion and said cover portion having means enabling the neck portion to be removably attached to the cover portion with the openings of the respective portions in alignment, whereby the user's protruding penis may extend into at least said neck portion to enable urine to be deposited directly into said urine-collecting portion of said pouch.

2. The device of claim 1 wherein said zipper extends to closely adjacent said neck portion whereby said zipper may be opened and the penis passed therethrough for normal urination into a receptacle.

3. The device of claim 1 wherein the attaching means comprises hook and loop connectors.

4. The device of claim 1 wherein the attaching means comprises snap fasteners.

5. The device of claim 1 wherein the attaching means comprises an annular flange surrounding said neck portion.

6. The device of claim 5 wherein said annular flange is flexible whereby the neck portion may be collapsed, passed through said cover opening from the exterior of said cover portion, said neck portion thereafter returning to its original shape to enable the flange to retain the pouch securely to said cover portion at least from the inside thereof.

7. The device of claim 1 wherein said strap member and cover portion comprise a conventional testicle-supporting suspensory device which encompasses a user's testicles and base of the penis by means of an elastic member immediately adjacent his body the cover portion of said suspensory device incorporating the frontal opening therein.

8. The device of claim 1 wherein said strap member is adjustable in length to accommodate male persons of different girths, and wherein said strap member is further provided with a means enabling the strap to be installed and replaced while said user is bedridden.

* * * * *